United States Patent
Chang

(10) Patent No.: US 6,676,673 B2
(45) Date of Patent: Jan. 13, 2004

(54) SURGICAL NEEDLE

(76) Inventor: Yu-Chung Chang, No.41, Ku Shan 3rd Road, Kaohsiung (TW)

( * ) Notice: Subject to any disclaimer, the term of this patent is extended or adjusted under 35 U.S.C. 154(b) by 93 days.

(21) Appl. No.: 09/971,963

(22) Filed: Oct. 5, 2001

(65) Prior Publication Data

US 2003/0036767 A1 Feb. 20, 2003

(30) Foreign Application Priority Data

May 25, 2001 (TW) .......................................... 90112719 A

(51) Int. Cl.[7] .............................................. A61B 17/04
(52) U.S. Cl. ...................................... 606/144; 606/139
(58) Field of Search ................................ 606/139, 145, 606/148, 144; 66/118; 128/98

(56) References Cited

U.S. PATENT DOCUMENTS

| | | | |
|---|---|---|---|
| 2,808,055 A | * 10/1957 | Thayer | 606/144 |
| 5,364,410 A | * 11/1994 | Failla et al. | 606/148 |
| 5,437,682 A | * 8/1995 | Grice et al. | 606/148 |
| 5,741,278 A | * 4/1998 | Stevens | 606/144 |
| 5,746,753 A | * 5/1998 | Sullivan et al. | 606/147 |

* cited by examiner

Primary Examiner—Kevin T. Truong

(57) ABSTRACT

The present invention relates a surgical instrument for performing hepatic resections, and the surgical instrument is called Chang's needle. The Chang's needle of the present invention comprises a stainless steel sheath and a stainless steel inner needle with a hook near the top of the inner needle. The advantageous features of the Chang's needle of the present invention are described as follows. The Chang's needle makes the hepatic resections safer and simplifies the surgical technique for hepatic resections thereby reducing the training time needed for surgeons. The Chang's needle is simple in mechanism, light and handy structure, small in size and low in price, and can be repeatedly sterilized and used. In addition to the traditional hepatic resections, the Chang's needle is suitable for use in segmental and partial hepactectomy of left lateral segment, and partial hepatectomies along the inferior border of the liver under a window with gasless-fashioned laparoscopic surgery.

10 Claims, 5 Drawing Sheets

SURGICAL NEEDLE

FIELD OF THE INVENTION

The present invention relates to a surgical instrument, more particularly, to a surgical instrument for performing hepatic resections, and the surgical instrument is called surgical needle.

BACKGROUND OF THE INVENTION

Liver is an organ filled with blood. There are three major issues that the operation of hepatic resection has faced, which are: temporarily blocking the blood vessels without causing anoxaemia; minimizing the blood loss; and determining the size of the portion of liver to be removed. The conventional methods commonly used for hepatic resections are: using Lin's Clamp invented by Prof. T. Y. Lin for achieving hemostasis by compression; fragmenting the liver parenchyma by the vibration from ultrasonic fluid with only reserving blood vessels and ligating the blood vessels thereafter; transecting the liver after clotting the blood in the blood vessels and tissue surrounding the top of needle by a microwave coagulator; and completing a resection after gelling the protein by the ultrahigh speed vibration with a Harmonic scapel and meanwhile achieving hemostasis.

Although the aforementioned methods popularly used for hepatic resections allow surgeons to complete the hepatic resections smoothly, yet each of the methods has its disadvantages and inconvenience respectively, wherein the shortcomings are, for example, increasing the training time needed for surgeons due to the complexity of surgical techniques; and utilizing the complicated and expensive instruments, etc.

SUMMARY OF THE INVENTION

Just as the aforementioned background of the invention, although these conventional methods of hepatic resections allow surgeons to complete the hepatic resections smoothly, yet each of the methods has its disadvantages and inconvenience respectively, and thus the training time needed for surgeons is increased, and the instruments used are complicated and expensive, etc.

Hence, one of the objects of the present invention is to provide a surgical needle for performing hepatic resections more safely, thereby contributing to the well-beings of the patients worldwide.

Another object of the present invention is to provide a surgical needle for simplifying the surgical technique of hepatic resection, and further reducing the training time needed for surgeons, so that the non-specialized general surgeons are also able to perform hepatic resections in a simple and safe way, and accordingly, the hepatic resections can be performed more commonly in the whole world.

A further object of the present invention is to provide a surgical needle, and the surgical needle is simple in mechanism, light and handy, small in size and low in price.

A further object of the present invention is to provide a surgical needle, and the surgical needle can be repeatedly sterilized and used.

According to the aforementioned objects of the present invention, the present invention thus provides a surgical needle, and the surgical needle comprises a stainless steel sheath and a stainless steel inner needle with a hook near the top of the inner needle. Utilization of surgical needle in the hepatic resections can make the procedures or right hepatic lobectomy, left lateral segmentectomy and some segmental or partial hepatectomy simpler and safer. While being applied, the surgical needle penetrates the whole depth of liver parenchyma to the bottom of liver from a certain liver surface location along both sides of a predetermined division line. Then, one end of a hemostatic suturing thread is caught with the hook near the top of the inner needle and brought up to the surface of liver from the bottom of liver. Thereafter, the surgical needle penetrates again to the bottom of liver from another liver surface loction that is at the same side with the previous penetrated location, and the other end of the suturing thread is caught with the hook and brought up to the surface of liver from the bottom of liver. Then, the two ends of the suturing thread are tied with a knot. After two rows of interlocking mattresses sutures are formed by repeating the aforementioned steps for a number of times. Subsequently, the liver parenchyma can be transected along the middle of these two interlocking mattress sutures without or with minimal bleeding. Hence, the application of the surgical needle in hepatic resections can simplify the surgical techniques and shorten the surgical time, while reducing ischemic injury and the blood loss during the hepatic surgery.

BRIEF DESCRIPTION OF THE DRAWINGS

The foregoing aspects and many of the attendant advantages of this invention will become more readily appreciated as the same becomes better understood by reference to the following detailed description, when taken in conjunction with the accompanying drawings, wherein.

DETAILED DESCRIPTION OF THE PREFERRED EMBODIMENT

The present invention is a surgical instrument used for hepatic resections, and the instrument is called a surgical needle. The mechanical structure of surgical needle is first described in the below and then the operation method thereof follows.

Figure 1A:
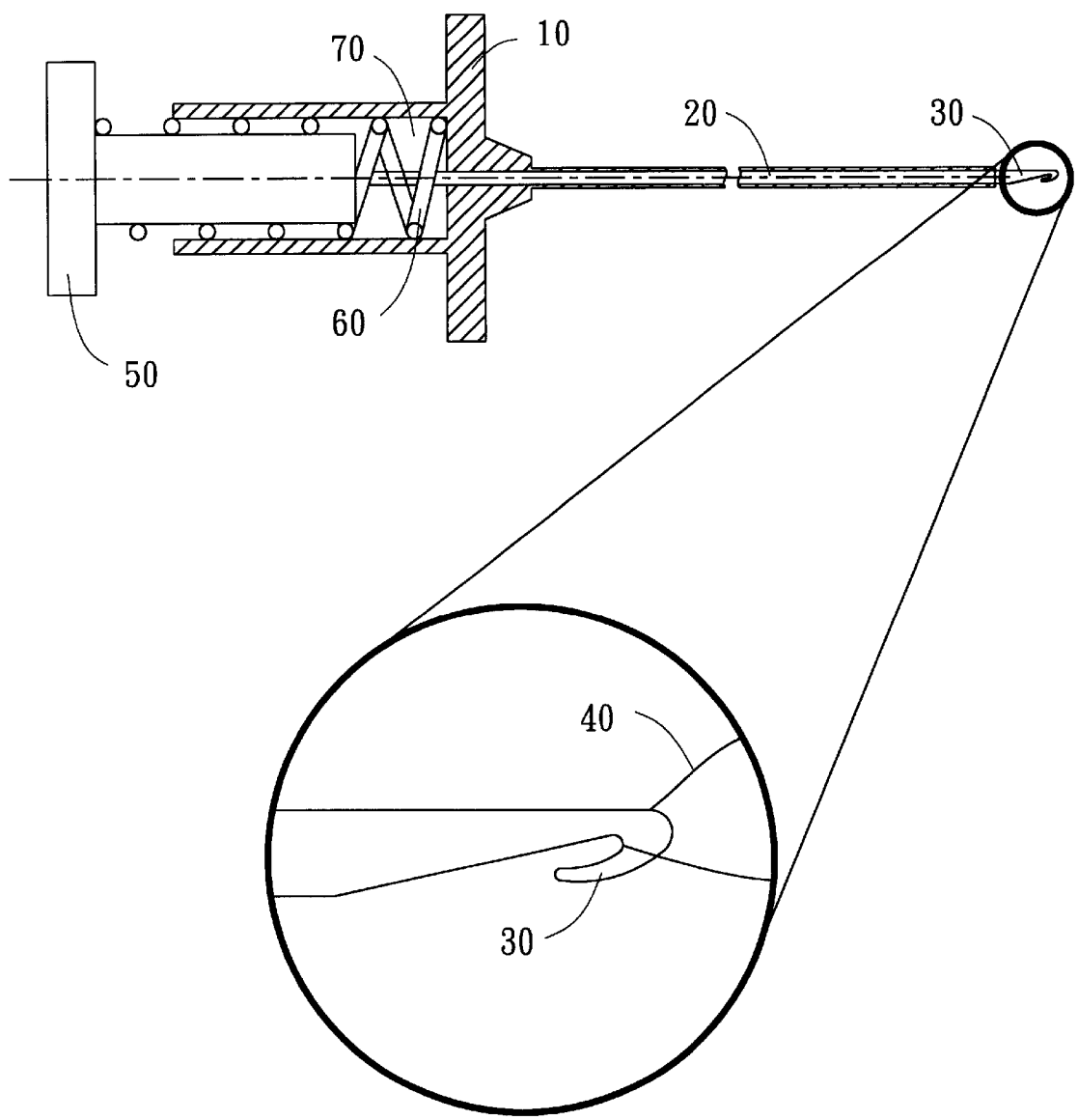
FIG. 1A is a diagram illustrating the details of a surgical needle and the local enlargement of the portion near the top of the inner needle according to the preferred embodiment of the present invention.

Referring to FIG. 1A, a preferred embodiment of a surgical needle of the present invention comprises a sheath 10 and an inner needle 20, and the inner needle 20 is inserted into the sheath 10 while the Chang's needle is applied. Both the sheath 10 and the inner needle 20 are made of stainless steel, but are not limited thereto. The length of the sheath 10 is about 17 cm, and that of the inner needle 20 is longer than that of the sheath 10 and is about 18 cm. There is a hook with a sharp tip 30 near the top of the inner needle to catch a suturing thread 40. While the inner needle 20 is inserted into one end of the sheath 10, for preventing the inner needle 20 from slipping out of the other end of the sheath 20, the design of a plunger 50 is implemented on the end away from the hook 30 of the inner needle 20. Besides, the surgical needle further comprises the design of an elastic member, and the elastic member can be, for example, a spring 60 or other articles having the elasticity, but the present invention is not limited thereto. The spring 60 is installed in the gap 70 between the inner needle 20 and the sheath 10, also is between the sheath 10 and the plunger 50, so that the hook 30 is hidden, but the sharp tip still remains outside the sheath, in sheath 10 when the spring 60 is neither compressed nor elongated, and the hook 30 is exposed outside sheath 10 when spring 60 is compressed.

Figure 1B:
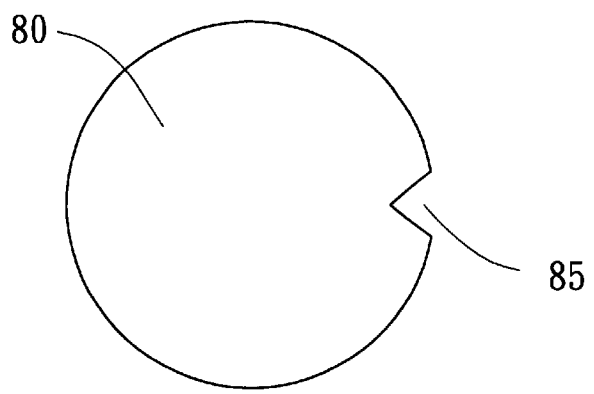
FIG. 1B is another view of the plunger of the stainless steel inner needle inside a surgical needle according to the preferred embodiment of the present invention, wherein the plunger has a groove.
Figure 1C:
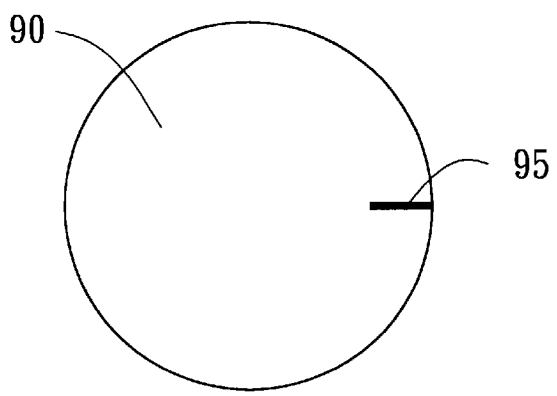
FIG. 1C is another view of the plunger of the stainless steel inner needle inside a surgical needle according to the preferred embodiment of the present invention, wherein the plunger has a notch.
Figure 1D:
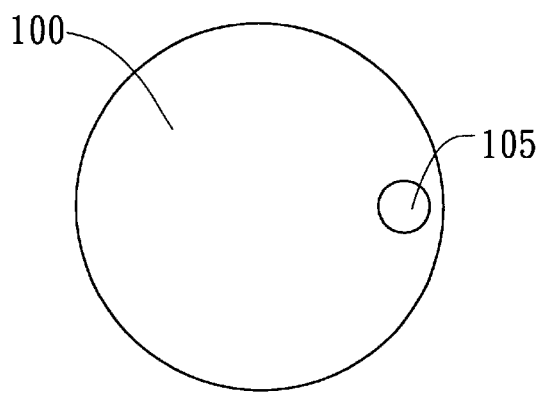
FIG. 1D is another view of the plunger of the stainless steel inner needle inside a surgical needle according the preferred embodiment of the present invention, wherein the plunger has a protuberance.

Furthermore, referring to FIG. 1B, for indicating the direction in which the hook hidden in the sheath faces or under the liver, the plunger 80 has the design of a groove 85, wherein the hook 30 is in the same direction with the groove 85. Except the design of groove 85, there are other designs which can also achieve the same function, for example, a notch 95 on the plunger 90 as shown in FIG. 1C and a protuberance 105 on the plunger 100 as shown in FIG. 1D.

Figure 2A:
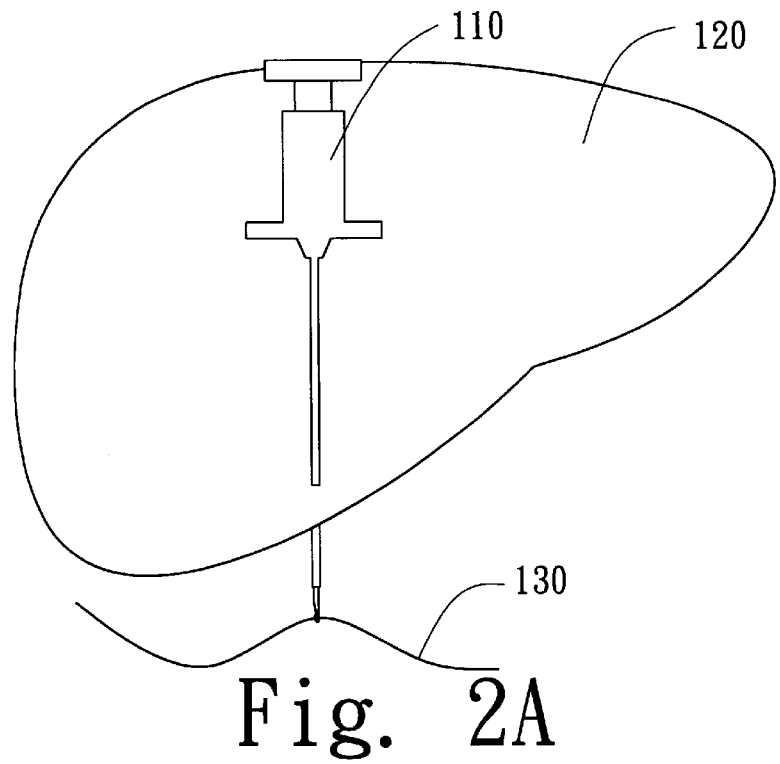
FIG. 2A is a schematic view showing the operation method of a surgical needle according to the preferred embodiment of the present invention, wherein the surgical needle has penetrated into the bottom of liver and caught one end of a suturing thread.
Figure 2B:
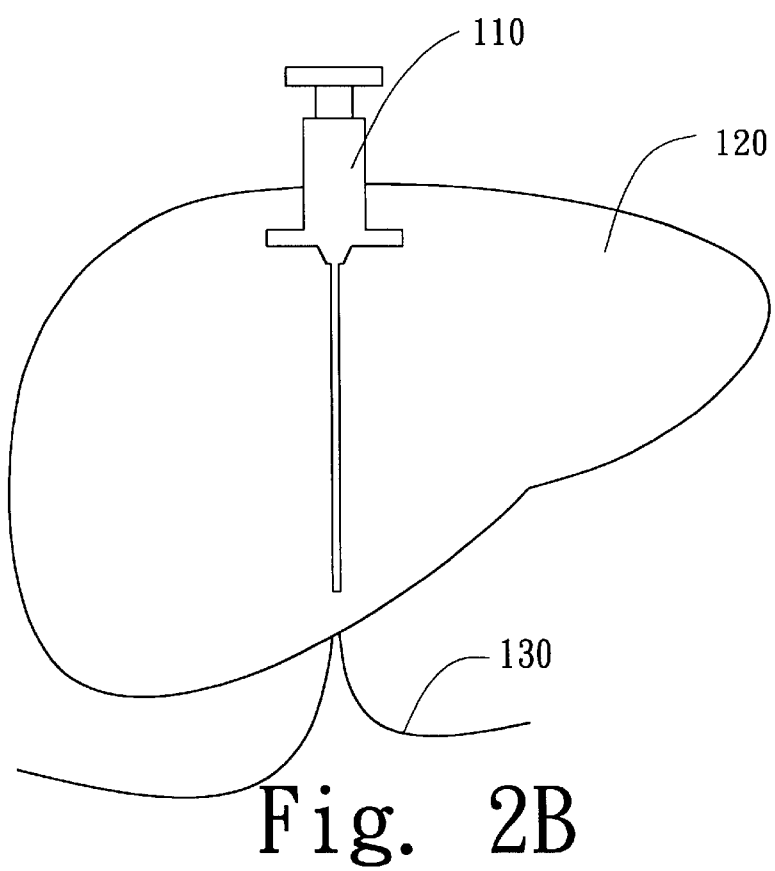
FIG. 2B is another schematic view showing the operation method of a surgical needle according to the preferred embodiment of the present invention, wherein the suturing thread has been bringing up to the surface of liver by pulling out the surgical needle from the bottom of liver.

The operation method of a surgical needle is described as follows. After the abdomen is opened with a proper method, the ligaments surrounding the portion of liver to be transected have to be cut off. Then, by pushing down the surgical needle while holding the inner needle and outer sheath together, the surgical needle penetrates vertically into the bottom of liver from the surface of liver, and catches one end of a suturing thread with a hook while the plunger of the inner needle is further pushed down, wherein the suturing thread can be made of No. 1 silk but not limited thereto. FIG. 2A is a schematic view showing the operation method of a surgical needle according to a preferred embodiment of the present invention, wherein the surgical needle 110 has penetrated into the bottom of liver 120 and caught a suturing thread 130 with a hook. Then, the hook is withdrawn into the sheath by releasing the plunger (as shown in FIG. 2B) so as to pull out surgical needle without harming or damaging the tubular structures inside the liver, and thereafter the portion of suturing thread has been pulled outside the surface of liver. FIG. 2B is another schematic view showing the operation method of a surgical needle according the preferred embodiment of the present invention, wherein the suturing thread 130 has been bringing out to the surface of liver 120 by pulling out the surgical needle 110.

Figure 2E:
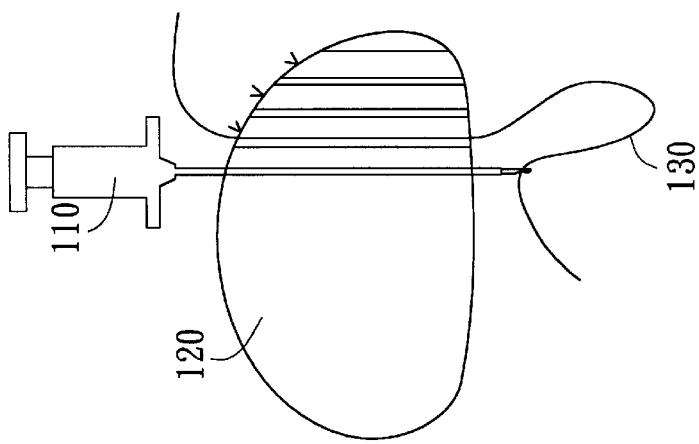
FIG. 2E is another schematic view showing the operation method of a surgical needle from another direction according to the preferred embodiment of the present invention. The diagram is a cross-sectional view of a surgical needle penetrating again into the bottom of liver and catching the other end of the suturing thread. Then, two ends of the suturing thread are tied with a knot after this procedure.
Figure 2D:
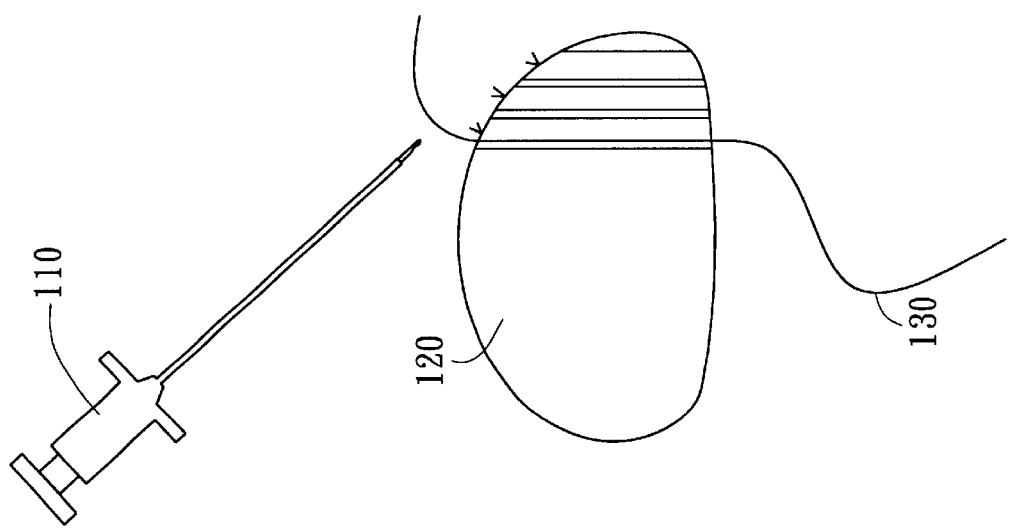
FIG. 2D is another schematic view showing the operation method of a surgical needle from another direction according to the preferred embodiment of the present invention, wherein the liver shown is a cross-sectional view, and the surgical needle has brought one end of the suturing thread to the surface of liver.
Figure 2C:
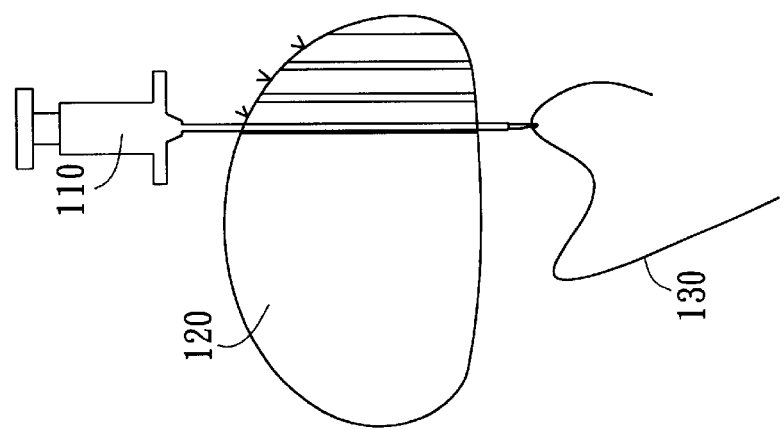
FIG. 2C is another schematic view showing the operation method of a surgical needle from another direction according to the preferred embodiment of the present invention, wherein the liver shown in a cross-sectional view, and the surgical needle has penetrated into the bottom of liver and caught one end of a suturing thread.

Thereafter, the aforementioned step for penetrating the surgical needle into the liver is repeated, and the locations penetrated currently and previously are on the same side of the predetermined division line, but are apart from 2 cm to 3 cm. After the surgical needle penetrates, the other end of the suturing thread is caught by a hook and pulled out to the surface of liver. Then, two ends of the suturing thread on the liver surface are tied with a knot and thereby the blood vessels within the range of suturing thread are totally ligated. FIG. 2C is another schematic view showing the operation method of a surgical needle from the other direction according to the preferred embodiment of the present invention, wherein the liver 120 is illustrated with a cross-sectional view, and the surgical needle 110 has penetrated into the bottom of liver 120 and caught one end of a suturing thread 130 with a hook. FIG. 2D is also another schematic view showing the operation method of a surgical needle from the other direction, wherein the liver 120 is illustrated with cross-sectional view, and the surgical needle 110 has brought up on end of a suturing thread 130 to the surface of liver 120. FIG. 2E is also another schematic view showing the operation method of a surgical needle from the other direction, wherein the liver 120 is illustrated with a cross-sectional view, and the surgical needle 110 has penetrated again into the bottom of liver 120 and caught the other end of a suturing thread 130 with a hook.

Figure 2F:
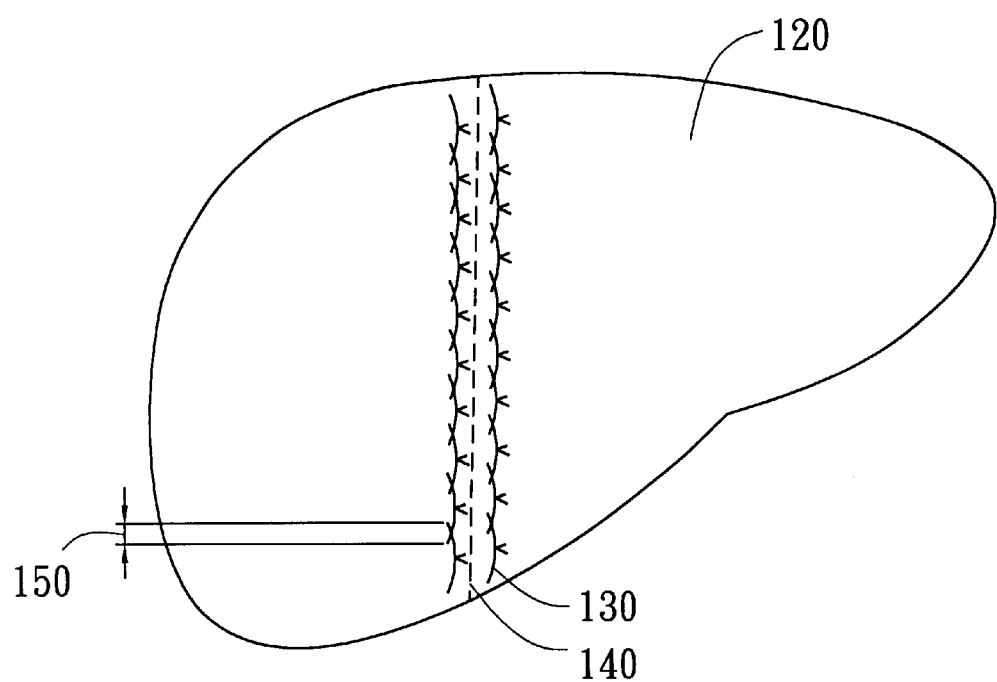
FIG. 2F is a diagram showing two rows of interlocked sutures by using a surgical needle according to the preferred embodiment of the present invention.

After the aforementioned steps are repeated for a plurality of times along two sides of the predetermined divisional line, the interlocking sutures are formed along two sides of the predetermined divisional line for the whole liver parenchyma. Referring to FIG. 2F, FIG. 2F is diagram showing two rows of finished interlocking sutures by using a surgical needle according to the preferred embodiment of the present invention, wherein two rows of interlocking sutures have been completed with a plurality of suturing threads 130 along two sides of the predetermined divisional line 140 on the liver 120. Furthermore, in order to firmly ligate all the related blood vessels as many as possible, two adjacent suturing threads 130 located on the same side of the predetermined divisional line 140 have to be properly interlocked. The length of the inter lock 150 is about, for example, 0.5 cm to 1 cm.

Thereafter, along the predetermined divisional line in the middle of two rows of suturing threads, the liver parenchyma is divided by electrocautery with minimal hemorrhage. For the safe's sake, during the operation of resection, the bigger blood vessels encountered are suture-ligated repeatedly for reinforcement.

In September 1997, the surgical needle was first successfully applied on the right hepatic lobectomy in Taiwan (R.O.C.), and the patient in this case was a cirrhotic hepatocellular carcinoma (HCC) patient, and only minimal blood loss is caused during the operation. From then on, there were 43 cases as shown in Table 1, wherein 19 HCCs, 4 cholangiocarcinomas (CCC), 4 colon metastases, 1 angiomyolipoma, 1 hemangioma, 1 liver trauma and 13 intrahepatic duct (IHD) stones, and the hepatic resections performed includes 9 right lobectomies, 5 bisegmentectomies, 7 segmentectomies, 4 subsegmentectomies, 2 partial hepatectomies, 15 left lateral segmentectomies and one hepatorrhapy. Ten patients had mild to severe degrees of liver cirrhosis (LC), one patient had chronic active hepatitis, two patients had liver fibrosis, and the other 30 patients had a normal liver. However, two of the four patients with CCC showed marked cholestasis, and one of these showed signs of sepsis before the operation.

Table 1 lists the 43 cases using the surgical needle of the present invention in Taiwan (R.O.C.). The scope of the present invention used in hepatic resections comprises: right lobectomy, right superior bisegmentectomy, right posterior bisegmentectomy, right posterosuperior segmentectomy, right posteroinfereior segmentectomy, right inferior bisegmentectomy, right partial hepatectomy, and left lateral segmentectomy or partial hepactectomy. Except for the aforementioned hepatectomies, this invention can also be used for segmental and partial hepactectomy of the left lateral segment, and partial hepatectomies along the inferior border of the liver under a window with gasless-fashioned laparoscopic surgery.

Another advantage of the present invention is to simplify the surgical technique for hepatic resections, and further to reduce the training time needed for surgeons. Thus, the non-specialized general surgeons are also able to perform hepatic resections easily, so that hepatic resections can be more popular all over the world.

Another advantage of the present invention is that the surgical needle is simple in mechanism, light and handy, small in size and low in price.

Another advantage of the present invention is that the surgical needle can be repeatedly sterilized and used.

As is understood by a person skilled in the art, the foregoing preferred embodiments of the present invention are illustrations of the present invention rather than limitations of the present invention. It is intended to cover various modifications and similar arrangements included within the spirit and scope of the appended claims, and the scope of which should be accorded with the broadest interpretation so as to encompass all such modifications and similar structures.

What is claimed is:

1. A surgical needle structure suitable for use in hepatic resections, and the surgical needle structure comprising:

TABLE 1

Patient's backgrounds and results of using surgical needle

| Cases | Primary Diseases | Associated Liver Diseases | Operation | Blood Loss (ml) | Procedure Related Morbidity | Remarks |
|---|---|---|---|---|---|---|
| 2 | HCC | mild LC | Rt. Lobectomy | minimal | no | |
| 1 | HCC | mild LC | Rt. Lobectomy | 2200 | no | unsecured tie |
| 4 | HCC(14,10, 20,12 cm) | No | Rt. Lobectomy | 1100, 1500, 650,250 | no | upper/lower ⅓ not applied |
| 1 | CCC | No | Rt. Lobectomy | 500 | Bile leak | |
| 1 | IHD stone | No | Rt. Lobectomy | minimal | no | Atrophied liver |
| 1 | HCC | mod. LC | Bisegmentectomy | minimal | no | S7,8 |
| 2 | HCC | No | Bisegmentectomy | minimal | no | S5,6 |
| 1 | Colon Meta. | No | Bisegmentectomy | minimal | no | S7,8 |
| 1 | AML | no | Bisegmentectomy | Minimal | no | S7,8 |
| 2 | HCC | mod. LC | Segmentectomy | 100,150 | no | S6 |
| 1 | HCC | fibrosis | Segmentectomy | 100 | no | S7 |
| 1 | HCC | CAH | Segmentectomy | minimal | no | S6 |
| 2 | Colon Meta. | No | Segmentectomy | minimal | no | S7 |
| 1 | Hemangioma | No | Segmentectomy | 100 | no | S7 |
| 2 | HCC | Fibrosis/no | Subsegmentectomy | minimal | no | S6, S7 |
| 1 | HCC | Mild LC | Subsegmentectomy | 125 | no | S6–7 |
| 1 | CCC | Severe LC | Subsegmentectomy | minimal | no | S7 |
| 2 | HCC | Mild/mod. LC | Partial hepatectomy | Minimal | no | S6, S7 |
| 10 | IHD stone | No | LLS | minimal | 1,bile leak | 2,w'd infections |
| 2 | IHD stone | No | LLS | 75,300 | no | |
| 1 | CCC | Liver abscess | LLS | 1000 | no | Septic coagulopathy |
| 1 | CCC | No | LLS | 75 | no | |
| 1 | Colon Meta. | No | LLS | 350 | no | |
| 1 | Trauma | No | Hepatorrhapy, (rt.lobe) | minimal | no | died of other injuries |

AML: Angiomyolipoma; CAH: chronic active hepatitis; CCC: cholangiocarcinoma Colon Meta: colon metastasis; HCC: hepatocellular carcinoma; IHD: intra-hepatic duct; LC: liver cirrhosis; LLS: left lateral segmentectomy; mod: moderate; w'd: wound.

In short, the main advantage of the present invention is to provide a surgical needle, and the application of the surgical needle of the present invention can make hepatic resections safer thereby contributing to the well-beings of the patients worldwide.

an inner needle, wherein one end of the inner needle has a plunger and the other end of the inner needle has a hook;

a sheath, wherein the needle is in the sheath, and there is a gap between the inner needle and the sheath; and an elastic member, wherein the elastic member is installed into the gap between the inner needle and the sheath, and the hook is hidden inside the sheath when the elastic member is neither compressed or elongated, and the hook is exposed to the outside of the sheath when the elastic member is compressed;

wherein the inner needle is about 18 cm and the sheath is about 17 cm.

2. The surgical needle structure of claim 1, wherein the inner needle is made of stainless steel.

3. The surgical needle structure of claim 1, wherein the hook is located near the top of the inner needle.

4. The surgical needle structure of claim 1, wherein the plunger of the inner needle further comprises a groove, which is used to indicate the direction that the hook faces when the hook is hidden in under the sheath or when the hook has penetrated to the bottom of the liver, and preparing to catch the thread.

5. The surgical needle structure of claim 1, wherein the plunger of the inner needle further comprises a notch, which is used to indicate the direction that the hook faces when the hook is hidden in under the sheath or when the hook has penetrated to the bottom of the liver, and preparing to catch the thread.

6. The surgical needle structure of claim 1, wherein the plunger of the inner needle further comprises a protuberance, which is used to indicate the direction that the hook faces when the hook is hidden in under the sheath or when the hook has penetrated to the bottom of the liver, and preparing to catch the thread.

7. The surgical needle structure of claim 1, wherein the inner needle is made of stainless steel.

8. An operation of a surgical needle, comprising:

penetrating the surgical needle from a location of a surface on a liver into a bottom of the liver;

catching one end of suturing thread with a hook of the surgical needle and bringing up the end of the suturing thread to the surface of the liver, and keeping the end on the surface;

penetrating the Surgical needle from another location the surface of the liver into the bottom of the liver;

catching the other end of the suturing thread with the hook and bringing up the end of the suturing thread of the surface of the liver; and tying the one end of the suturing thread and the other end of the suturing thread with a knot;

wherein the location of the surface on the liver is at one side of a predetermined divisional line, and the other location is at the same side of the predetermined divisional line, and the other location is about 2 cm to 3 cm from the location.

9. The operation method of the surgical needle of claim 8, wherein the hook is located near a top of the inner needle.

10. The operation method of the surgical needle of claim 8, wherein the suturing thread is made of No. 1 silk or other suitable suture materials.

* * * * *